United States Patent
Amanuel et al.

(10) Patent No.: US 11,566,999 B2
(45) Date of Patent: Jan. 31, 2023

(54) SPECTRAL ANALYSIS OF GASSES EMITTED DURING ROASTING FOOD

(71) Applicants: Samuel Amanuel, Schenectady, NY (US); Palmyra Catravas, Rockville, MD (US); Joanne D Kehlbeck, Ballston Lake, NY (US)

(72) Inventors: Samuel Amanuel, Schenectady, NY (US); Palmyra Catravas, Rockville, MD (US); Joanne D Kehlbeck, Ballston Lake, NY (US)

(73) Assignee: Union College, Schenectady, NY (US)

( * ) Notice: Subject to any disclaimer, the term of this patent is extended or adjusted under 35 U.S.C. 154(b) by 249 days.

(21) Appl. No.: 16/392,851

(22) Filed: Apr. 24, 2019

(65) Prior Publication Data
US 2019/0323954 A1    Oct. 24, 2019

Related U.S. Application Data

(60) Provisional application No. 62/661,834, filed on Apr. 24, 2018.

(51) Int. Cl.
*G01N 21/3504* (2014.01)
*A23F 5/04* (2006.01)
(Continued)

(52) U.S. Cl.
CPC .......... *G01N 21/3504* (2013.01); *A23F 5/04* (2013.01); *G01N 21/65* (2013.01); *G01N 33/02* (2013.01); *G01N 2021/3595* (2013.01)

(58) Field of Classification Search
CPC .............. A23F 5/04; G01N 2021/3595; G01N 21/3504; G01N 21/65; G01N 33/02
See application file for complete search history.

(56) References Cited

U.S. PATENT DOCUMENTS

| 5,342,638 A | 8/1994 | Koch |
| 6,296,890 B1 | 10/2001 | Navarini et al. |

(Continued)

FOREIGN PATENT DOCUMENTS

| WO | 0064242 | 11/2000 | |
| WO | 2016038479 | 3/2016 | |
| WO | WO-2016142167 A1 * | 9/2016 | ........... A23N 12/125 |

OTHER PUBLICATIONS

Translation of WO2016142167A1, Keller, Marco, Sep. 15, 2016 (Year: 2016).*

(Continued)

*Primary Examiner* — Jill A Warden
*Assistant Examiner* — Henry H Nguyen
(74) *Attorney, Agent, or Firm* — Bond Schoeneck & King, PLLC; Joseph M. Noto

(57) ABSTRACT

A method for evaluating and controlling roasting and degree (level) of roast in food items including but not limited to: coffee, cocoa, beans, nuts, grains and seeds, involves collecting spectra of the gases (including water vapor) emitted during roasting in the mid-infrared region using either mid-infrared source or visible light to include Raman scattering. The changes in the spectra, due to absorption by molecular vibrations in the gases emitted during roasting are evaluated in real time during roasting. These data may be processed in frequency or time domain. The spectra and change in spectra are correlated with a roasting profile to mark the inception of roasting, progress of roasting and maturity/achievement of degree of a roast. The information can be transmitted to the roaster or controller to monitor the roasting progress and can be used to adjust parameters as desired during roasting.

12 Claims, 14 Drawing Sheets

(51) Int. Cl.
  *G01N 21/65* (2006.01)
  *G01N 33/02* (2006.01)
  *G01N 21/35* (2014.01)

(56) References Cited

U.S. PATENT DOCUMENTS

| | | | |
|---|---|---|---|
| 2002/0158202 A1* | 10/2002 | Webber | G01N 21/3504 250/339.13 |
| 2003/0048432 A1 | 3/2003 | Jeng et al. | |
| 2005/0065732 A1 | 3/2005 | Tilton et al. | |
| 2010/0009039 A1 | 1/2010 | Robinson et al. | |
| 2015/0320071 A1 | 11/2015 | Leloup et al. | |
| 2016/0120211 A1* | 5/2016 | Wilson | A23N 12/125 426/233 |
| 2017/0319002 A1* | 11/2017 | Tan | A23F 5/04 |
| 2018/0085003 A1* | 3/2018 | Goldring | A61B 5/0013 |

OTHER PUBLICATIONS

Alessandrini, Laura et al., "Near infrared spectroscopy: An analytical tool to predict coffee roasting degree", Analytica Chimica Acta 625 (2008); copyright 2008 Elsevier B.V.; pp. 95-102.
Craig, Ana Paula, et al., "Mid infrared spectroscopy and chemometrics as tools for the classification of roasted coffees by cup quality", Food Chemistry, vol. 245, Apr. 15, 2018, copyright 2018 Elsevier B.V.; pp. 1052-1061; Abstract provided.
El-Abassy, Rasha M., et al., "Discriminariton between Arabica and Robusta green coffee using visible micro Raman spectroscopy and chemometric analysis", Food Chemistry 2010, doi:10.1016/j.foodchem.2010.11.132; 6 pages.
Oliveira, Leandro S., et al., "Applications of Near Infrared Spectroscopy (NIRS) in Food Quality Evaluation", In: Food Quality: Control, Analysis and Consumer Concerns, copyright 2011 Nova Science Publishers, Inc.; pp. 131-179.
Wermelinger, Thomas, et al., "Quantification of the Robusta Fraction in a Coffee Blend via Raman Spectroscopy: Proof of Principle", Journal of Agricultural and Food Chemistry 2011, 59(17), pp. 9074-9079; publication date(web) Aug. 10, 2011; copyright 2011 American Chemical Society; Abstract provided.
Zhang, C., et al., "Application of Near-Infrared Hyperspectral Imaging with Variable Selection Methods to Determine and Visualize Caffeine Content of Coffee Beans", Food and Bioprocess Technology Jan. 2017, vol. 10, Issue 1, pp. 213-221; Abstract provided.
Santos et al. "Exploiting near infrared spectroscopy as an analytical tool for on-line monitoring of acidity during coffee roasting", Food Control, vol. 60. pp. 408-415, 2016.
Santos et al. "In-line monitoring of the coffee roasting process with near infrared spectroscopy: Measurement of sucrose and colour", Food Chemistry, vol. 208, pp. 103-110, 2016.
Wang, "Physicochemical Changes of Coffee Beans During Roasting", Thesis of Niya Wang, 2012.
Wang et al. "Feasibility Study on Chemometric Discrimination of Roasted Arabica Coffees by Solvent Extraction and Fourier Transform Infrared Spectroscopy", J. Agric. Food Chem. pp. 3220-3226, 2011.
Wang et al. "Fourier Transform Infrared and Physicochemical Analyses of Roasted Coffee", J. Agric. Food Chem. pp. 5446-5453, 2012.
Wang et al. "Effect of roasting conditions on carbon dioxide degassing behavior in coffee", Food Research International, vol. 61, pp. 144-151, 2014.
Catelani et al. "A Non-invasive Real-Time Methodology for the Quantification of Antioxidant Properties in Coffee During the Roasting Process Based on Near-Infrared Spectroscopy" Food Bioprocess Technol, vol. 10, pp. 630-638, 2017.
Yeretzian et al. "Progress on Coffee Roasting: A Process Control Tool for a Consistent Roast Degree—Roast After Roast" New Food, vol. 15, pp. 22-26, 2012.

Baggenstoss et al. "Coffee Roasting and Aroma Formation: Application of Different Time—Temperature Conditions" J. Agric. Food Chem., vol. 56, pp. 5836-5846, 2008.
Baggenstoss "Coffe Roasting and Quenching Technology—Formation and Stability of Aroma Compounds" pp. 1-151, Zurich, 2008.
Barbin et al. "Application of Infrared Spectral Techniques on Quality and Compositional Attributes of Coffee: An Overview" Food Research International, vol. 61, pp. 23-32, 2014.
Catelani et al. "Real-Time Monitoring of a Coffee Roasting Process with Near Infrared Spectroscopy using Multivariate Statistical Analysis: A Feasibility Study" Talanta, vol. 179, pp. 292-299, 2018.
Czech et al. "Resolving Coffee Roasting-Degree Phases Based on the Analysis of Volatile Compounds in the Roasting Off-Gas by Photoionization Time-of-Flight Mass Spectrometry (PI-TOFMS) and Statistical Data Analysis: Toward a PI-TOMFS Roasting Model" J. Agric. Food Chem., vol. 64, pp. 5223-5231, 2016.
Czerny et al. "Potent Odorants of Raw Arabica Coffee. Their Changes During Roasting" J. Agric. Food Chem., vol. 18, pp. 868-872, 2000.
Hertz-Schunemann et al. "On-Line Process Monitoring of Coffee Roasting by Resonant Laser Ionisation Time-Of-Flight Mass Spectrometry: Bring the Gap from Industrial Batch Roasting Flavor Formation Inside an Individual Coffee Bean" J. Mass Spectrom, vol. 48, pp. 1253-1265, 2013.
Hertz-Schunemann et al. "Looking into Individual Coffee Beans During the Roasting Process: Direct Micro-Probe Sampling On-Line Photo-Ionisation Mass Spectrometric Analysis of Coffee Roasting Gases" Anal Bioanal Chem., vol. 405, pp. 7083-7096, 2013.
Czech et al. "Supporting Information of Resolving coffee roasting-degree phases based on the analysis of volatile compounds in the roasting off-gas by photoionization time-of-flight mass spectrometry (PI-TOFMS) and statistical data analysis: Towards a PI-TOFMS roasting model", pp. 1-9.
Lyman et al. "FTIR-ATR Analysis of Brewed Coffee: Effect of Roasting Conditions", J. Agric. Food Chem., vol. 51, pp. 3268-3272, 2003.
Nicolotti et al. "Volatile Profiling of High Quality Hazelnuts (*Corylus avellana* L.): Chemical Indices of Roasting" Food Chemistry, vol. 138, pp. 17230-1733, 2013.
Pendergrast, "The History of Coffee and How it Transformed our World," Basic Books: New York (2010).
Luttinger, "The Coffee Book: Anatomy of an Industry From Crop to the Last Drop," Thew Press: New York (2006).
USDA, "Coffee: World Markets and Trade," Foreign Agricultural Service 1-9 (2016).
Illy et al., "Espresso Coffee: The Science of Quality," Second, ed., Illy Andrea and Viani Rinantonio, Elsevier Academic (2005).
Anagelo et al., "Numerical Model of Heat and Mass Transfer During Roasting Coffee Using 3D Digitised Geometry," Procedia Food Science 1:742-46 (2011).
Wang et al., "Fourier Transform Infrared and Physicochemical Analyses of Roasted Coffee," J. Agri. Food Chem, 60 (21):5446-53 (2012).
Wayner et al., "Effect of the Roasting Process on Glass Transition and Phase Transition of Colombian Arabic Coffee Beans," Procedia Food Science, 1:385-90 (2011).
El-Abassy et al., "Discrimination Between Arabica and Robusta Green Coffee Using Visible Micro Raman Spectroscopy and Chemometric Analysis," Food Chemistry 126 (3): 1443 8 (2011).
Wilson, "Coffee Roasting Acoustics," The Journal of Acoustical Society of America, 35 (6):EL265-9 (2014).
Pohl et al., "Determination of the Elemental Composition of Coffee Using Instrumental Methods," Food Analytical Methods 6 (2):598-613 (2013).
Schenker, Investigations on the Hot Air roasting of coffee beans, Doctoral Thesis, Swiss Federal Institute of Technology (ETH): Zurich (2000).
Ruosi et al., "A Further Tool to Monitor the Coffee Roasting Process: Aroma Composition and Chemical Indices. Journal of Agricultural and Food Chemistry," 60(45): 11283-91 (2012).

(56) References Cited

OTHER PUBLICATIONS

Wei et al., "Roasting Process of Coffee Beans as Studied by Nuclear Magnetic Resonance: Time Course of Changes in Composition," Journal of Agricultural and Food Chemistry, 60(4):1005-12 (2012).

Baggenstoss et al., "Coffee Roasting and Aroma Formation: Application of Different Time-Temperature Conditions," Journal of Agricultural and Food Chemistry, 56(14):5836-46 (2008).

Hashim et al., "Use of Methylpyrazine Ratios to Monitor the Coffee Roasting," Food Research International, 28(6) 319-623(1995).

Nehring et al., "Indirect Determination of the Degree of Roast in Coffee," Zeitschrift fur Lebensmittel und-forschung. 195(1):39-42 (1992).

Zhou et al. "Effect of Heat Treatment on the Content of Individual Phospholipids in Coffee Beans," Food Chemistry, 141(4):3846-50 (2013).

Mills et al., "The effect of Processing on Chlorogenic Acid Content of Commercially Available Coffee," Food Chemistry, 141(4):3335-40 (2013).

Kumazawa et al., "Identification of Odor-Active 3-Mercapto-3-methylbutyl Acetate in Volatile Fraction of Roasted Coffee Brew Isolated by Steam Distillation under Reduced Pressure," Journal of Agricultural and Food Chemistry 51 (10):3079-82 (2003).

Dias et al., "Roasting Process Affects the Profile of Diterpenes in Coffee," European Food Research Technology, 239 (6):961-70 (2014).

Dorfner et al., "Laser Mass Spectrometry as On-Line Sensor for Industrial Process Analysis: Process Control of Coffee Roasting," Analytical Chemistry 76(5): 1386-1402 (2004).

Hertz-Schünemann et al., "On-line Process Monitoring of Coffee Roasting by Resonant Laser Ionisation Time-of-Flight Mass Spectrometry: Bridging the Gap from Industrial Batch Roasting to Flavour Formation Inside an Individual Coffee Bean," Journal of Mass Spectrometry. 48(12): 1253-65 (2013).

Hertz-Schunemann Romy et al., "Looking into Individual Coffee Beans During the Roasting Process: Direct Micro-probe Sampling on-line Photo-ionisation Mass Spectrometric Analysis of Coffee Roasting Gases," Analytical and Bioanalytical Chemistry, 405(22):7083-96 (2013).

Barbin et al., "Application of Infrared Spectral Techniques on Quality and Compositional Attributes of Coffee: An Dverview," Food Research International, 61:23-32 (2014).

Ioannou et al., "Real Time Monitoring the Maillard Reaction Intermediates by HPLC-FTIR," Journal of Physical Chemistry and Biophysics, 6(2):6-10 (2016).

Dias Rafael Carlos Eloyet al., "Investigating Coffee Samples by Raman Spectroscopy for Quality Control—Preliminary Study," International Journal of Experimental Spectroscopic Techniques, 1(2):1-5 (2016).

Briandet et al., "Discrimination of Arabica and Robusta in Instant Coffee by Fourier Transform Infrared Spectroscopy and Chemometrics," Journal of Agricultural and Food Chemistry 44:170-4 (1996).

Esteban-Díez et al., "An Evaluation of Orthogonal Signal Correction Methods for the Characterisation of Arabica and Robusta Coffee Varieties by NIRS," Analytica Chimica Acta, 514(1):57-67 (2004).

Craig et al., "Application of Elastic net and Infrared Spectroscopy in the Discrimination Between Defective and Non-Defective Roasted Coffees," Taianta, 128:393-400 (2014).

Craig et a., "Fourier Transform Infrared Spectroscopy and Near Infrared Spectroscopy for the Quantification of Defects in Roasted Coffees," Taianta, 134:379-86 (2015).

Pizarro et al., "Influence of Data Pre-Processing on the Quantitative Determination of the Ash Content and Lipids in Roasted Coffee by Near Infrared Spectroscopy," Analytica Chimica Acta, 509(2):217-27 (2004).

Alessandrini et al., "Near Infrared Spectroscopy: An Analytical Tool to Predict Coffee Roasting Degree," Analytica Chimica Acta, 625(1):95-102 (2008).

Croasmun et al., "Gas Chromatography-Matrix Isolation Infrared Spectroscopy-Mass Spectrometry for Analysis of Thermally Generated Aroma Compounds,". Thermal Generation of Aromas, Editors; American Chemical Society Symposium Series, Washington, DC, 409:61-71 (1989).

Moon et al., "Role of Roasting Conditions in the Level of Chlorogenic Acid Content in Coffee Beans: Correlation with Coffee Acidity," Journal of Agricultural and Food Chemistry, 57(12):5365-9 (2009).

Basile et al., "A Lumped Specific Heat Capacity Approach for Predicting the Non-stationary Thermal Profile of Coffee During Roasting," Chemical and Biochemical Engineering Quarterly, 23(2): 167-77 (2009).

Hernández, "Analysis of the Heat and Mass Transfer During Coffee Batch Roasting," Journal of Food Engineering, 78 (4):1141-8 (2007).

Wang et al., "Effect of Roasting Conditions on Carbon Dioxide Degassing Behavior in Coffee," Food Research International, 61:144-51 (2014).

Schenker et al., "Pore Structure of Coffee Beans Affected by Roasting Conditions," Journal of Food Science, 65 (3):452-457 (2000).

Tressl Roland et al., "Investigation of Sulfur-Containing Components in Roasted Coffee," Journal of Agricultural and Food Chemistry, 29(5):1078-82 (1981).

\* cited by examiner

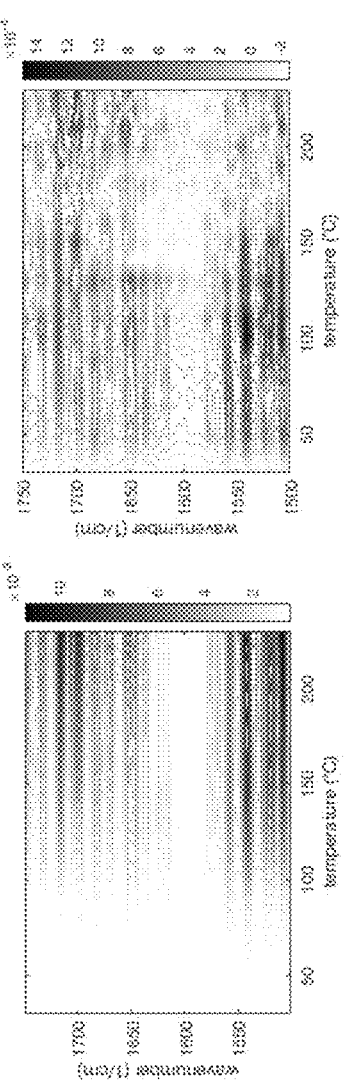
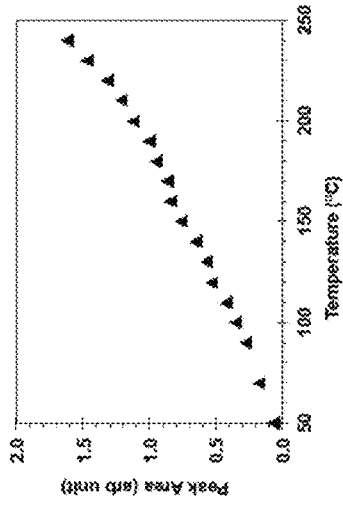
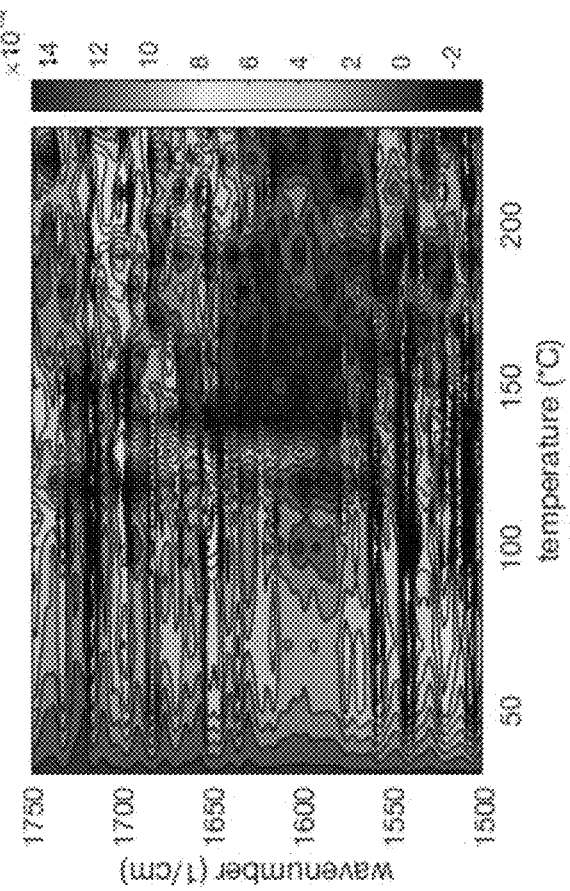
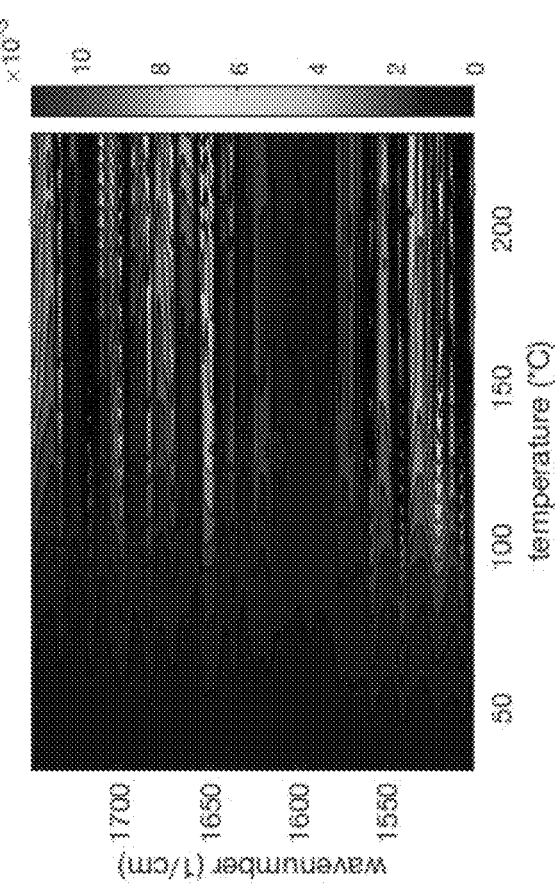
FIG. 14A  FIG. 14B  FIG. 14C  FIG. 14D  FIG. 14E

SPECTRAL ANALYSIS OF GASSES EMITTED DURING ROASTING FOOD

CROSS REFERENCE

This application claims the benefit of the filing date of U.S. Provisional Patent Application Ser. No. 62/661,834, filed Apr. 24, 2018 which is hereby incorporated by reference in its entirety.

FIELD

The present invention relates generally to the roasting of food items, and more specifically to real-time process and system control of roasting food items by monitoring of the evolved gases and their interaction with electromagnetic radiation.

BACKGROUND

Roasting is a critical step in food processing that significantly influences the quality of the final product. For example, the widespread consumption of coffee did not take a foothold until roasting was introduced, even though it was discovered much earlier in the southern highlands of Ethiopia. Currently, about two billion cups are consumed daily throughout the world. During roasting, the beans change in color, expand and contract, lose weight and moisture, and emit volatile organic compounds. Because these physical changes are correlated with the chemical reactions, artisans employ these physical changes as roasting markers. For instance, the "first crack" is commonly used to mark the beginning of light roast while the "second crack" is commonly associated with the transition from light to dark roast. These in conjunction with changes in visual appearance, such as change in color and luster, are widely used to classify the degree of a roast. These markers, however, are subjective and inherent differences in the beans limit their efficacy. Arabica beans appear more glossy than Robusta beans because of their greater lipid content. The differences in the beans cause also differences in the number of cracks. While an ensemble of beans crack twice as a chorus, some beans crack more than twice and yet other beans do not crack at all. In industrial settings, temperature profiles are heavily used to develop a desired roast. Temperature profile alone, however, cannot ensure the consistency of the desired roast due to variation in the beans and their moisture content.

Employing analytical techniques in conjunction with these common practices can improve the consistency of a roast. Baggenstoss Juerg; Poisson Luigi; Kaegi Ruth; Perren Rainer; Escher Felix. Coffee Roasting and Aroma Formation: Application of Different Time—Temperature Conditions. Journal of Agricultural and Food Chemistry. 2008, 56 (14), 5836-5846 (Baggenstoss et al.) studied the evolution of water content, density and lightness (L) in conjunction with formation of aroma compounds and demonstrated that lightness is a better indicator of roast than time alone. Hashim Laih; Chaveron Henri. Use of methylpyrazine ratios to monitor the coffee roasting. Food Research International. 1995, 28 (6), 619-623 (Hashim and Chaveron) suggest that the alkylpyrazine can be used to monitor degree of roasting. Hashim and Chaveron suggest that the ratio of 2-methylpyrazine to 2,5-dimethylpyrazine or ratio of 2-methylpyrazine to 2,6-dimethylpyrazine can be used as marker for roasting. Similarly, Nehring Ulrich P.; Maier Hans Gerhard. Indirect determination of the degree of roast in coffee. Zeitschrift für Lebensmittel und-forschung. 1992, 195 (1), 39-42 (Nehring and Maier) used capillary gas chromatography to quantify the alanine, leucine, phenylalanine content in roasted beans in order to indirectly calculate the organic roasting loss (ORV) during roasting. In general, darker roasts have lower level of phospholipids, chlorogenic acids, 3-mercapto-3-methylbutyl esters but higher amounts of cafestol and kahweol. Over-roasting, however, degrades the cafestol and kahweol.

Molecular vibrations have been used to monitor Maillard reactions in food and to study coffee specifically. Most of the studies on coffee, however, have focused on quality control to identify defects in beans and discriminate bean cultivar. El-Abassy Rasha M.; Donfack, Patrice; Materny Arnulf. Discrimination between Arabica and Robusta green coffee using visible micro Raman spectroscopy and chemometric analysis. Food Chemistry. 2011, 126 (3), 1443-1448 (El-Abassy et al.) used micro-Raman spectroscopy to discriminate Arabica green beans from Robusta green beans. Briandet Romain; Kemsley E. Katherine; Wilson Reginald H. Discrimination of Arabica and Robusta in Instant Coffee by Fourier Transform Infrared Spectroscopy and Chemometrics. Journal of Agricultural and Food Chemistry. 1996, 44,170-174 (Briandet et al.) showed diffuse reflectance infrared Fourier transform (DRIFT) spectroscopy and attenuated total reflectance (ATR) can be used to distinguish Arabica from Robusta in instant coffee. Esteban-Díez Isabel; González-Sáiz José Maria; Pizarro Millán C. An evaluation of orthogonal signal correction methods for the characterisation of arabica and robusta coffee varieties by NIRS. Analytica Chimica Acta. 2004, 514 (1), 57-67 (Esteban-Diez, Gonzalez-Saiz and Pizarro) used near infrared (NIR) spectra to distinguish Arabica from Robusta beans. Craig Ana Paula; Franca Adriana S.; Oliveira Leandro Soares; Irudayaraj Joseph; Ileleji Klein. Application of elastic net and infrared spectroscopy in the discrimination between defective and non-defective roasted coffees. Talanta. 2014, 128, 393-400 (Craig et al. 2014) studied vibrational bands from carbohydrates, amino acids, lipids, caffeine and chlorogenic acid in roasted coffee beans using attenuated total reflectance Fourier transform infrared (ATR-FTIR) spectroscopy and NIR in order to distinguish defective from non-defective beans. Craig Ana Paula; Franca Adriana S.; Oliveira Leandro Soares; Irudayaraj Joseph; Ileleji Klein. Fourier transform infrared spectroscopy and near infrared spectroscopy for the quantification of defects in roasted coffees. Talanta. 2015, 134,379-386 (Craig et al. 2015) claim that the models from the NIR measurements are robust in quantitatively discerning adulterated coffee grounds from defective beans. Few infrared (IR) studies have focused on using the technique to identify degree of roast. NIR has been used to correlate ash and lipid content with degree of roast. Similarly, absorbance in the NIR has been correlated with color, weight, density and moisture content to predict roasting degree in Arabica, Robusta and mixtures of Arabica and Robusta beans. Because of scattering, however, interpretation of the NIR spectra is difficult without doing significant data processing. Lyman Donald J.; Benck Robert; Dell Stacy; Merle Scott Murray-Wijelath Jacqueline. FTIR-ATR Analysis of Brewed Coffee: Effect of Roasting Conditions. Journal of Agricultural and Food Chemistry. 2003, 51 (11), 3268-3272 (Lyman et al.) used FTIR-ATR to study the effect of roasting conditions on the flavor-print in brewed coffee and found that the type and concentration of the carbonyl compounds formed during roasting depends on the roasting conditions. A major drawback of these techniques is that the analyses take a long time and the information cannot be provided in real-time during roasting. Alternatively, time of flight mass spectrometry (TOFMS) of the volatile organic compounds (VOC) emitted during roasting of coffee beans has been useful in providing real-time information during roasting.

SUMMARY

In accordance with one aspect of the present disclosure, there is provided a method for roasting a food item, including:

heating a food item over time sufficient to obtain a desired flavor that accompanies physical and chemical changes in the food item, including the emission of gases;

subjecting the emitted gases to electromagnetic radiation;

measuring the interaction of the electromagnetic radiation with the emitted gases as a function of a roasting parameter to detect the spectral changes that accompany roasting;

comparing the spectral changes that occur during a specific roasting profile in order to identify the points that mark at least one of the inception of roasting, progress of roasting and maturity of roasting; and adjusting at least one of the roasting parameters to achieve a desired roast of the food item based on the spectral data detected.

These and other aspects of the present disclosure will become apparent upon a review of the following detailed description and the claims appended thereto.

BRIEF DESCRIPTION OF THE DRAWINGS

FIG. 7A shows a contour plot of the raw mid-IR absorption spectra, while

FIG. 14A is a graph of the intensity of the absorption as calculated from the area under the peaks between 1726 and 1691 cm-1 for Example 2, FIG. 14B and FIG. 14D show the contour plot of the intensity of the absorption for each wavenumber bin as a function of temperature, and FIG. 14C and FIG. 14E show the derivative of the intensity with respect to temperature, which improves the discernment of multiple signatures in the spectrum, including the onset of roasting over FIGS. 14A, 14B and 14D for the background subtraction method used in Example 2.

DETAILED DESCRIPTION

Figure 1:
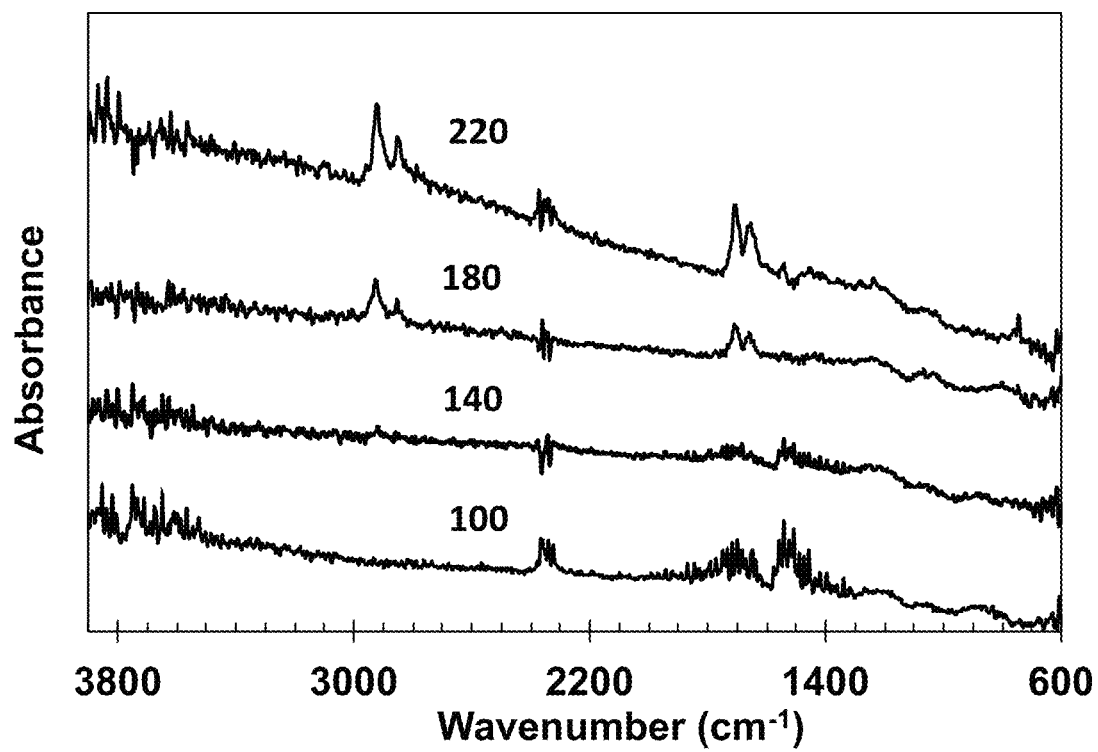
FIG. 1 is a series of mid-IR absorption spectra of the gases emitted during roasting with the temperatures indicated in ° C.

The present invention is directed to a method for marking the inception of roasting, progress of roasting and maturity and achievement of degree of a roast in food items including but not limited to: coffee, cocoa, beans, nuts, grains and seeds, from the mid-IR spectra of the gases emitted during roasting. The present invention involves the use of mid-IR sources directed to the gases emitted during roasting. The changes in spectra due to absorption by the molecular vibrations in the gases are correlated individually or in tandem with each other with roasting parameters and degree of roast in the food items. The profile of these changes is correlated with a pre-described roasting profile to mark the inception of roasting, progress of roasting and maturity of the roasting.

The method for roasting a food item includes heating a food item over time sufficient to obtain a desired flavor that accompanies physical and chemical changes in the food item, including the emission of gases.

Another aspect of the invention uses a visible light source and a detector to probe the gases emitted during roasting using Raman scattering. The changes in spectra due to absorption by the molecular vibrations in the gases are correlated individually or in tandem with each other with roasting parameters and degree of roast in the food items. The profile of these changes is correlated with a pre-described roasting profile to mark the inception of roasting, progress of roasting and maturity of the roasting.

Aspects of the invention include evaluating the intensity of the signals between 1726 cm-1 and 1690 cm-1, to mark the inception of roasting, level of a roast, progress of roasting and maturity/achievement of degree of a roast of food items.

Aspects of the invention include evaluating the intensity of the signals between 2200 cm-1 and 2000 cm-1, to mark the inception of roasting, level of a roast, progress of roasting and maturity/achievement of degree of a roast of food items.

Aspects of the invention include evaluating the intensity of the signals between 3000 cm-1 and 2800 cm-1, to mark the inception of roasting, level of a roast, progress of roasting and maturity/achievement of degree of a roast of food items.

Aspects of the invention include evaluating the intensity of the signals between 3500 cm-1 and 3100 cm-1, to mark the inception of roasting, level of a roast, progress of roasting and maturity/achievement of degree of a roast of food items.

Another aspect of the invention includes the use of mid IR measurements of emitted gases during roasting to provide calibration information for other sensors and diagnostic outputs that can be used to mark the inception of roasting, level of a roast, progress of roasting and maturity/achievement of degree of a roast of food items.

Another aspect of the invention includes the use mid IR measurements of emitted gases during roasting to mark the inception of roasting, progress of roasting and maturity/achievement of degree of a roast and provide fiducial information in tandem with other sensors.

The foregoing has outlined in general how the molecular vibrations in the gasses emitted during roasting can be used to mark the inception of roasting, level of a roast, progress of roasting and maturity/achievement of degree of a roast of food items.

The present invention relates generally to the roasting of food items, and more specifically, to real-time process and system control of coffee roasting by monitoring the evolved gases and their absorption in the mid infrared radiation. The present invention correlates mid-IR spectral analysis of gases emitted during roasting in real time with a roasting profile in food items (including but not limited to: coffee, cocoa, beans, nuts, grains and seeds) that mark the inception of roasting, progress of roasting and maturity/achievement of degree of a roast.

During roasting of food items different gases (including water vapor) are released at different stages of the roasting. The present invention probes the gases using a mid-infrared and visible electromagnetic radiation source and detects what is transmitted, reflected, and diffusely scattered. Part of the radiation is absorbed due to the molecular vibrations and the strength of the absorption is due to the gaseous products formed during roasting and is correlated with roasting parameters of the food items and degree of roast in the food items.

The disclosure will be further illustrated with reference to the following specific examples. It is understood that these examples are given by way of illustration and are not meant to limit the disclosure or the claims to follow.

Example 1: FTIR spectra were collected in a reflection mode using a Hyperion microscope (Bruker) with mercury cadmium telluride (MCT) detector. We collected 64 scans with 4 cm$^{-1}$ resolution. Four Yirga Chefe green beans (2 with their seam up and 2 with their seam down) were placed in a modified heating (Linkam) stage where a thin metallic foil was used to reflect the IR beam. The beans were placed in such a way that they did not to block any part of the IR beam. Temperature of the stage was raised at 10° C. per minute and was held isothermally for 4 minutes at each prescribed temperature. As soon the temperature reached the set point, a spectrum was collected and background was collected before the temperature was raised.

FIG. 1 is a series of mid-IR absorption spectra of the gases emitted during roasting. The spectra are collected in reflection mode with the temperatures indicated. Arabica coffee beans were used in this experiment.

Figure 2:
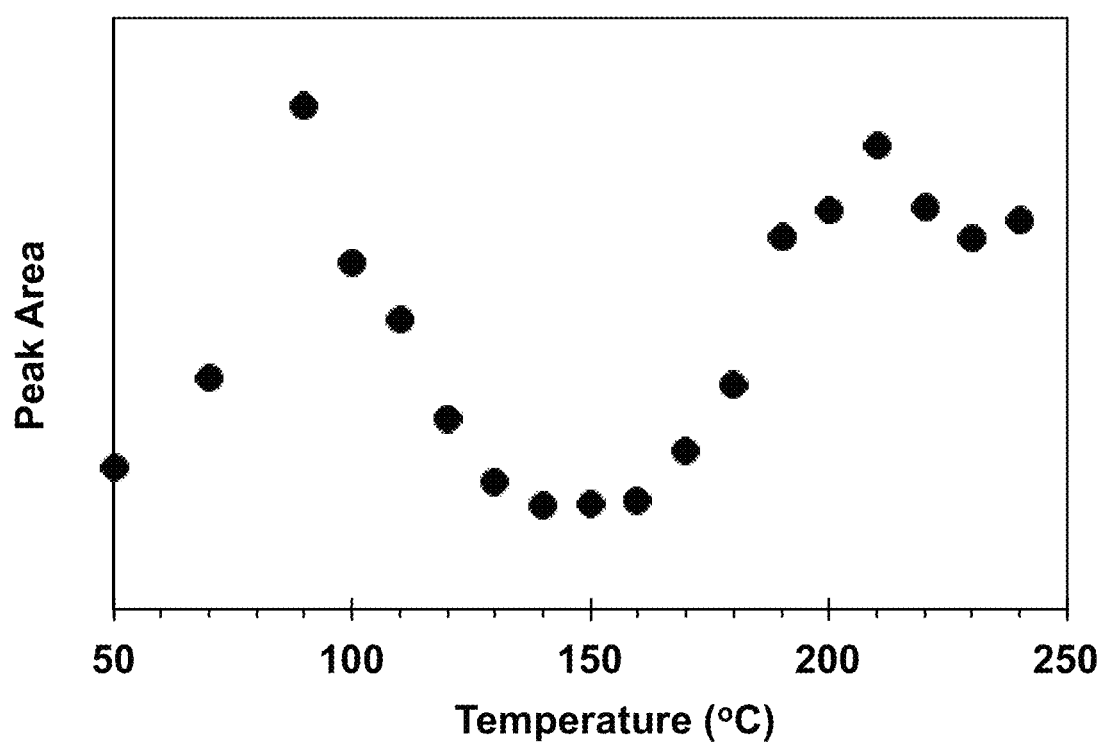
FIG. 2 is a graph of the intensity of the absorption as calculated from the area under the peaks between 1726 and 1691 cm-1.

FIG. 2 is a graph of the intensity of the absorption as calculated from the area under the peaks between 1726 and 1691 cm-1.

Figure 3:
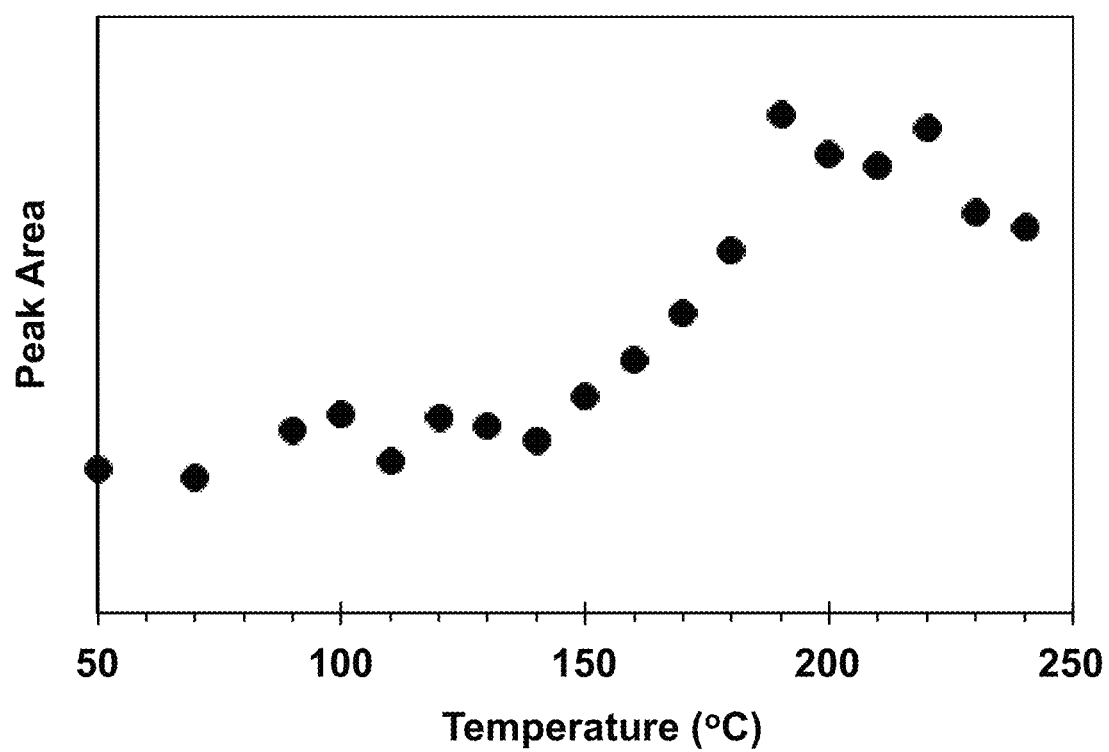
FIG. 3 is a graph of the intensity of the absorption as calculated from the area under the peaks between 2985 and 2831 cm-1.

FIG. 3 is a graph of the intensity of the absorption as calculated from the area under the peaks between 2985 and 2831 cm-1.

Figure 4:
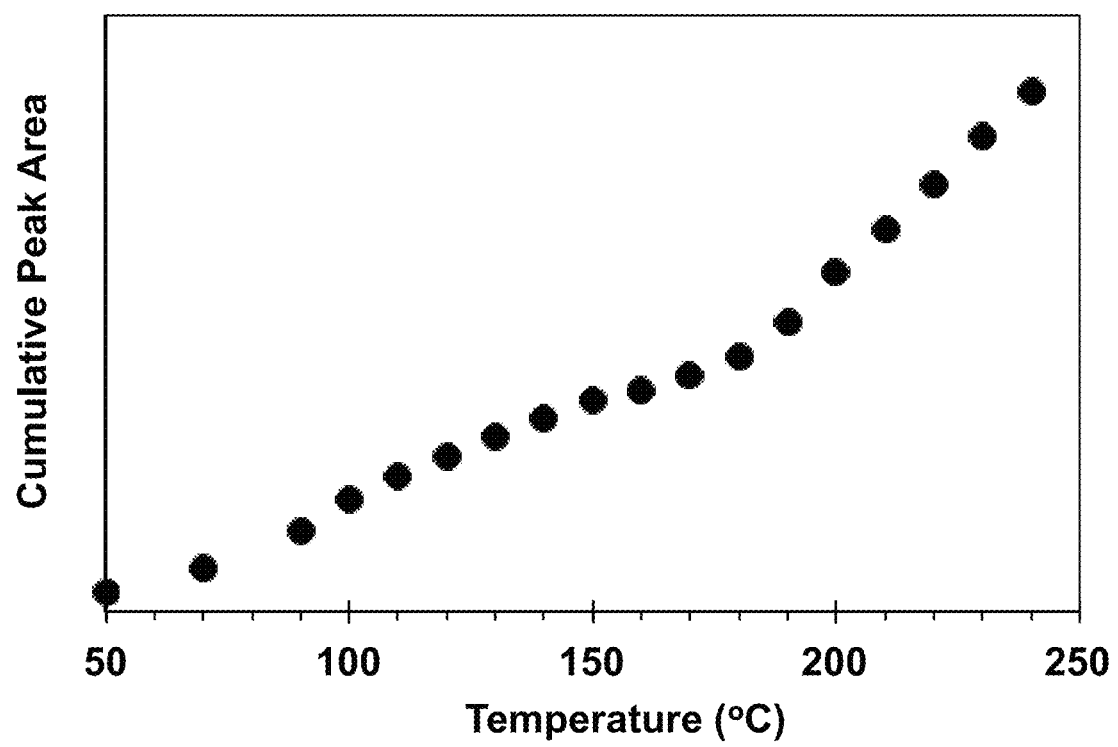
FIG. 4 is a graph of the cumulative intensity of the absorption as calculated from the sequential sum of areas in FIG. 2.

FIG. 4 is a graph of the cumulative intensity of the absorption as calculated from the sequential sum of areas in FIG. 2.

Figure 5:
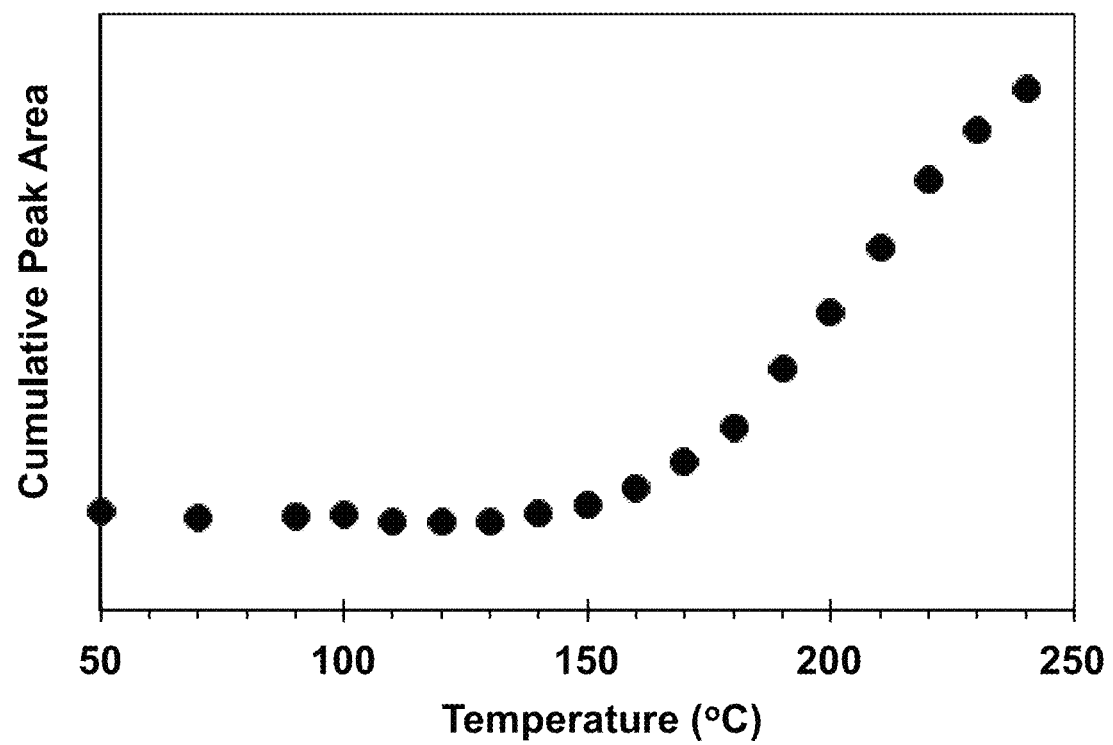
FIG. 5 is a graph of the cumulative intensity of the absorption as calculated from the sequential sum of areas in FIG. 4.

FIG. 5 is a graph of the cumulative intensity of the absorption as calculated from the sequential sum of areas in FIG. 4.

For instance, FIG. 1 presents absorbance spectra collected at different temperatures during roasting of Arabica coffee. These spectra have been shifted vertically for the clarity of presentation. However, they have not been modified in any other way. The multiple sharp peaks in the two regions of 3800-3500 cm-1 and 1850-1350 cm-1 are indicative of water vapor released at different stages. Because the vapors do not readily escape from the roasting chamber, they condense and form droplets along the beam path. This causes Mie scattering and can manifest as uneven vertical shift in the absorbance spectra. Coffee beans with significant (initial) water content cause significant scattering in comparison to coffee beans that are dry. This is more pronounced at lower temperatures when most of the bulk water is released from the beans.

The intensity of absorption due to molecular vibrations can be used as a roasting marker. The intensity of several vibrational bands from the area under the peak was calculated. FIG. 2 shows how the intensity of the signals between 1726 and 1691 cm$^{-1}$ changes with temperature where there are two maxima as a function of temperature. The first is due to drying of the beans whereas the maximum at higher temperature is due to roasting of the beans. The onset of the second maximum and its levels mark the inception of roasting, level of a roast, progress of roasting and maturity/achievement of degree of a roast.

FIG. 3 shows how the intensity of the signals between 2985 and 2831 cm$^{-1}$ changes with temperature where there is rapid increase in intensity above 150° C. This marks the inception of roasting and its values indicate the level of a roast, progress of roasting and maturity/achievement of degree of a roast.

Because we collected background at each set temperature, another way of looking at the intensity is by looking at the cumulative area of the peaks. FIG. 4 shows the cumulative area of the between 1726 and 1691 cm$^{-1}$ which was obtained by sequentially adding the areas in FIG. 2. The intensity as presented in FIG. 4 increases with the temperature, however, the rate of increase is different at different temperatures. Fast increase is obtained above 150° C., which indicates inception of roasting. The values of the intensity indicate the level of a roast, progress of roasting and maturity/achievement of degree of a roast.

Similarly, FIG. 5 shows the cumulative area of the between 2985 and 2831 cm$^{-1}$ which was obtained by sequentially adding the areas in FIG. 3. The intensity as presented in FIG. 5 increases rapidly above 150° C., which indicates inception of roasting. The values of the intensity indicate the level of a roast, progress of roasting and maturity/achievement of degree of a roast.

The intensity of absorption due to molecular vibrations individually or in tandem with each other indicates inception of roasting, level of a roast, progress of roasting and maturity/achievement of degree of a roast.

Visualization of the signals and of functions of the signals as they change with temperature across a roast enables rapid, holistic evaluation of the evolution of the diagnostic features of the signals and is useful for comparing one roast with another. The signals may be separated into two components—the uneven vertical shift of the spectra and the net absorption spectra after baseline removal—for a global view of correlated, complementary diagnostic information they contain. One example of the implementation of a holistic view of the roasting process is a contour plot of each component of the mid IR signal resolved in wavenumber/frequency to show the morphological signature of variations across and within clusters of peaks as they evolve with temperature or other roasting parameter. Another example is a contour plot of the cumulative signal, resolved in wavenumber. Another example is a contour plot of the derivative of the spectra with respect to temperature or other roasting parameter. Contour plots of the derivative of the spectra with respect to temperature are useful when examining regions of the spectrum where multiple signatures are present and, depending on the method of background subtraction used, can improve the discernment of the separate signatures and the onset of roasting.

FIG. 6 through FIG. 9 shows additional complementary spectra and their contour plots from the same experimental setup and run as that described in Example 1. However, each spectrum in these cases was collected two minutes after the temperature reached it is set point and before a background was collected.

Figure 6:
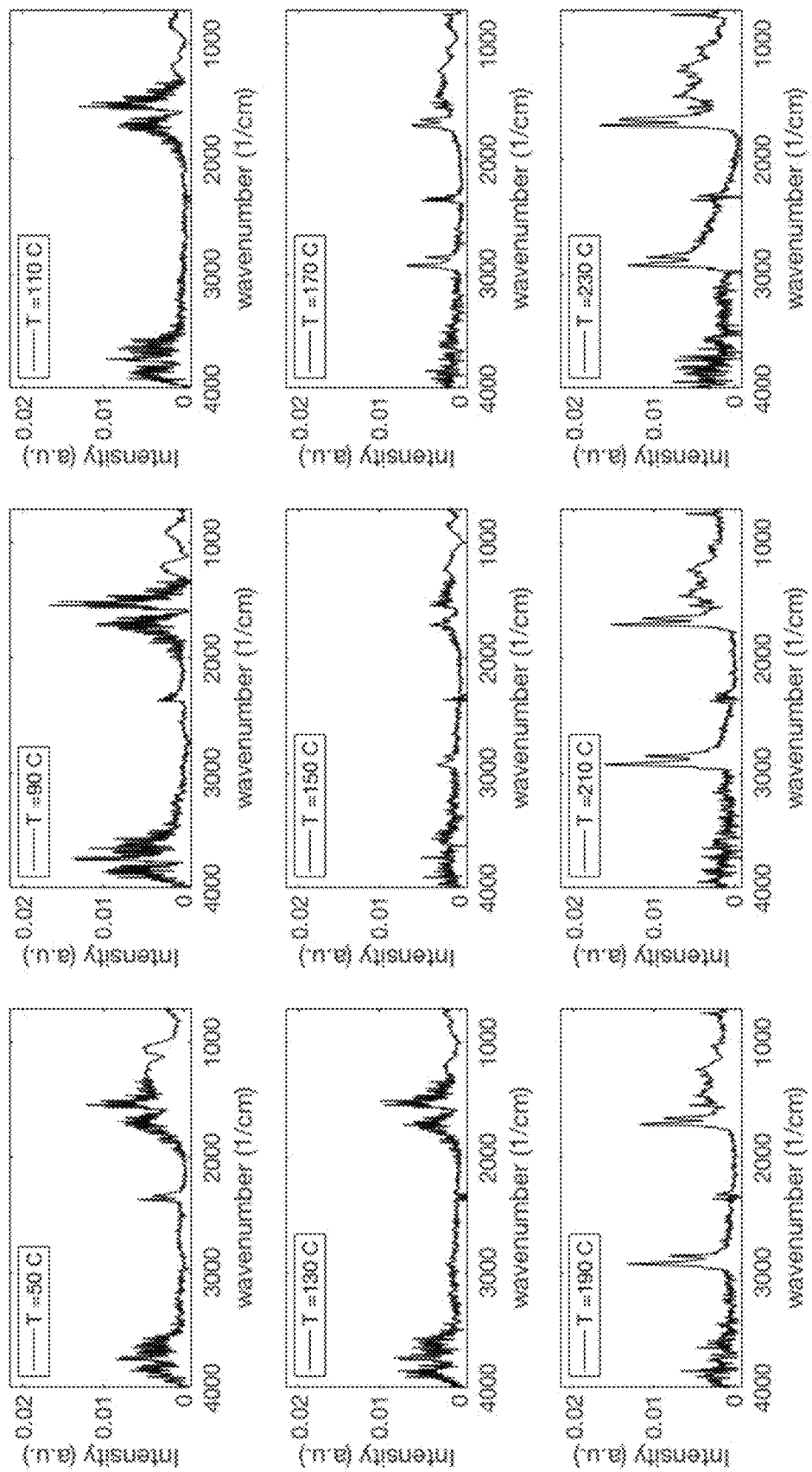
FIG. 6 is the sequence of mid-IR absorption spectra at different temperatures of the gases emitted during roasting after baseline removal of the even vertical shift for each spectrum.

FIG. 6 is the sequence of mid-IR absorption spectra at different temperatures of the gases emitted during roasting after removal of the even vertical shift for each spectrum. Polynomial fitting was used for baseline removal.

Figure 7A:
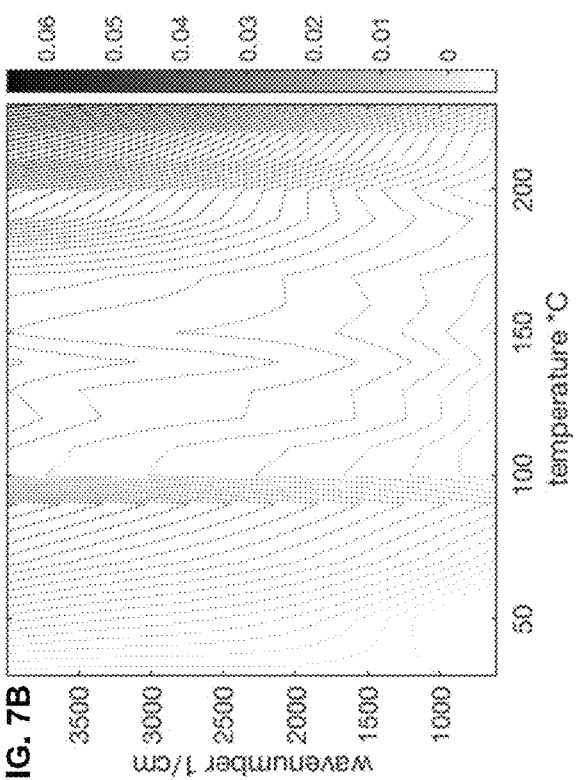
Figure 7B:
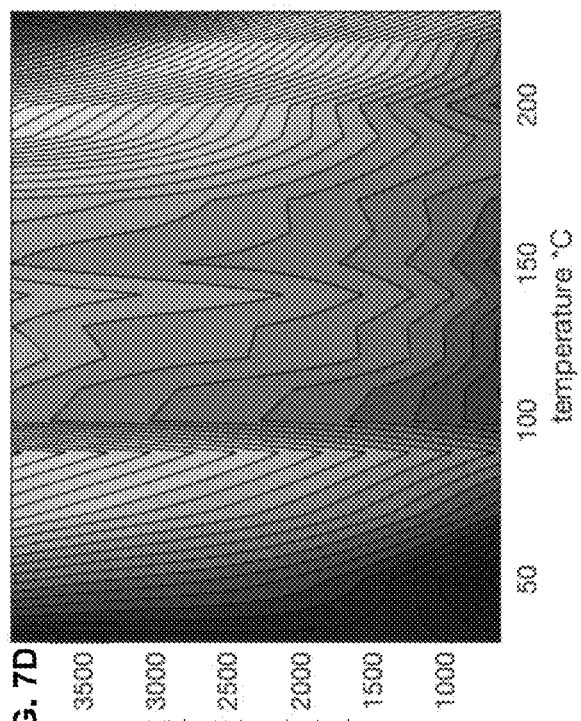
FIG. 7B shows the global evolution of the uneven vertical shift of the spectra across the temperature range from 30° C. to 240° C. and color versions of the greyscale plots in FIGS. 7A and 7B are shown in FIGS. 7C and 7D, respectively.
Figure 7C:
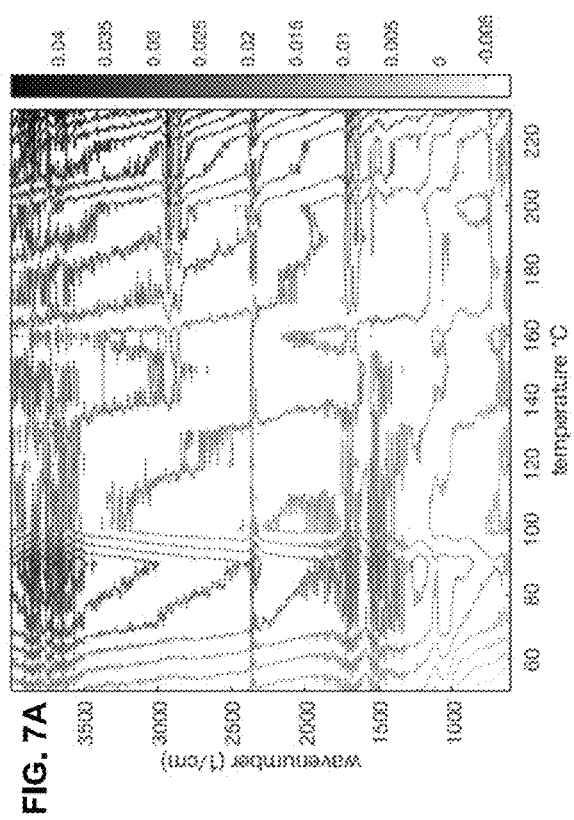
Figure 7D:
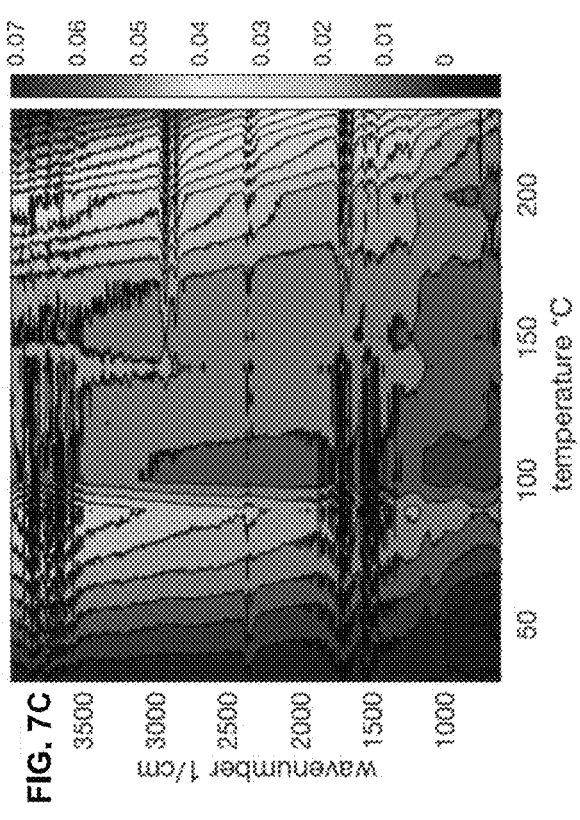

FIG. 7A shows a contour plot of the full series of mid-IR absorption spectra and FIG. 7B shows the global evolution of the uneven vertical shift of the spectra across the full roast of the four bean sample. Color versions of the greyscale plots in FIGS. 7A and 7B are shown in FIGS. 7C and 7D, respectively.

Figure 8A:
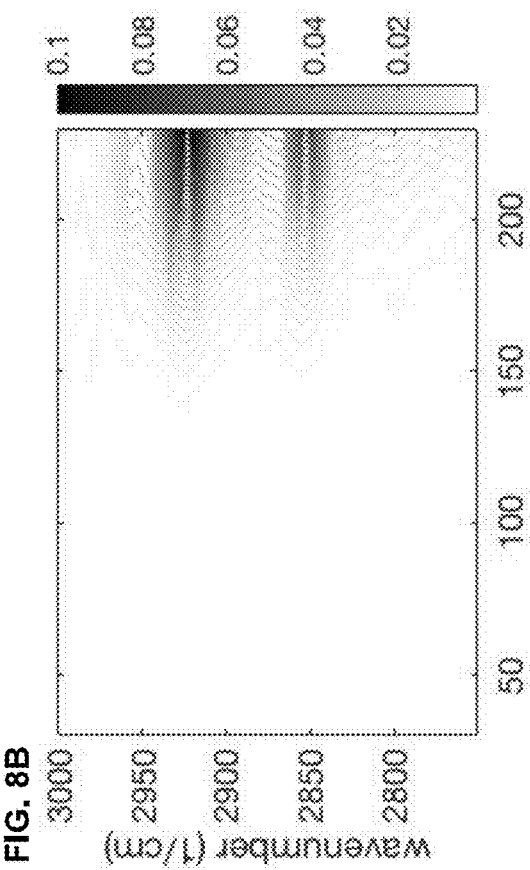
FIG. 8A shows a contour plot of the absorption spectra (intensity vs heating stage temperature and wavenumber), along with FIG. 8B, the cumulative signal resolved in each wavenumber bin between 3000 and 2750 cm-1, with color versions provided in FIGS. 8C and 8D.
Figure 8B:
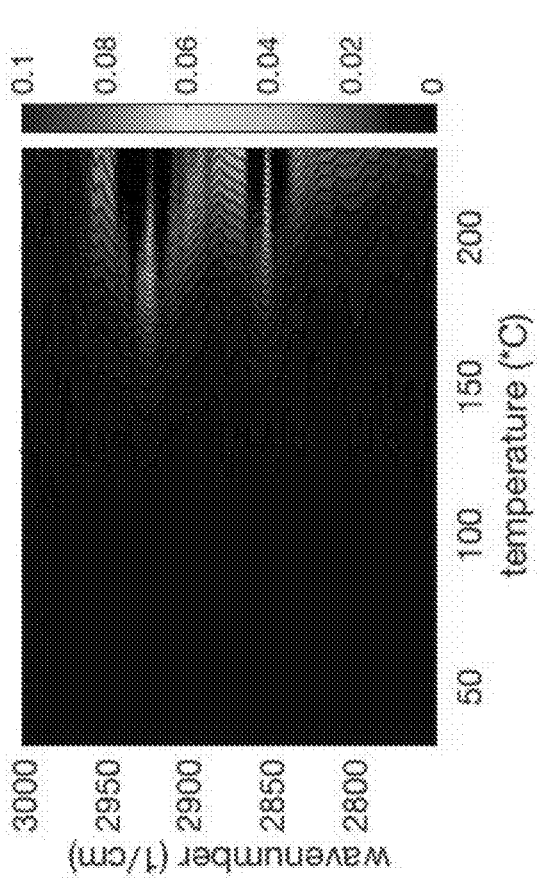
Figure 8C:
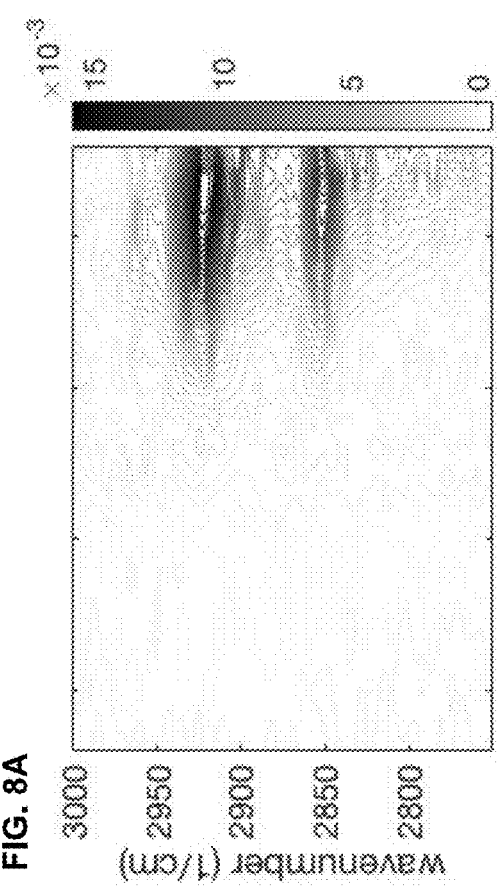
Figure 8D:
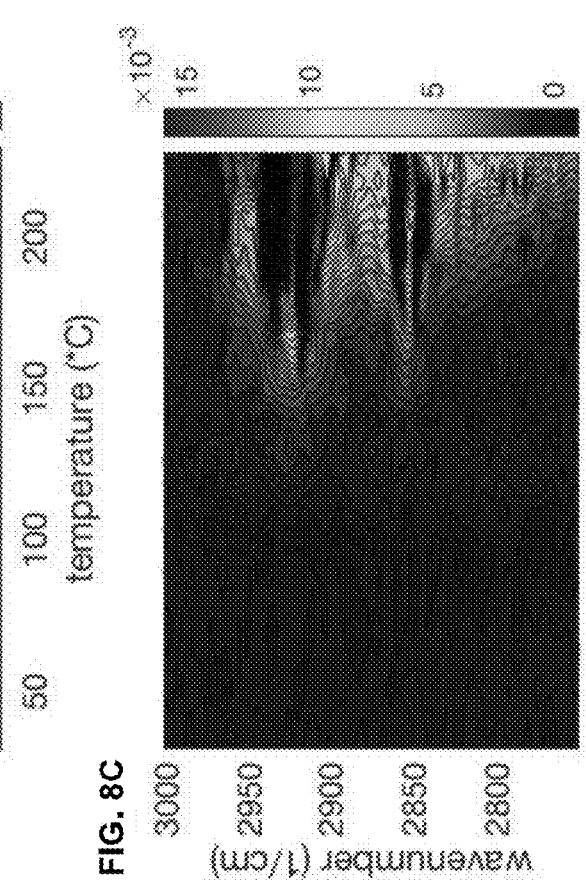

FIG. 8A shows a contour plot of the absorption spectra (intensity vs heating stage temperature and wavenumber), along with FIG. 8B, the cumulative signal resolved in each wavenumber bin, corresponding to the wavenumber range of FIG. 3. The detailed morphologies of the spectral peaks crossed with a roasting parameter viewed with high resolution permits. Color versions of FIG. 8A and FIG. 8B are shown in FIG. 8C and FIG. 8D, respectively.

Figure 9A:
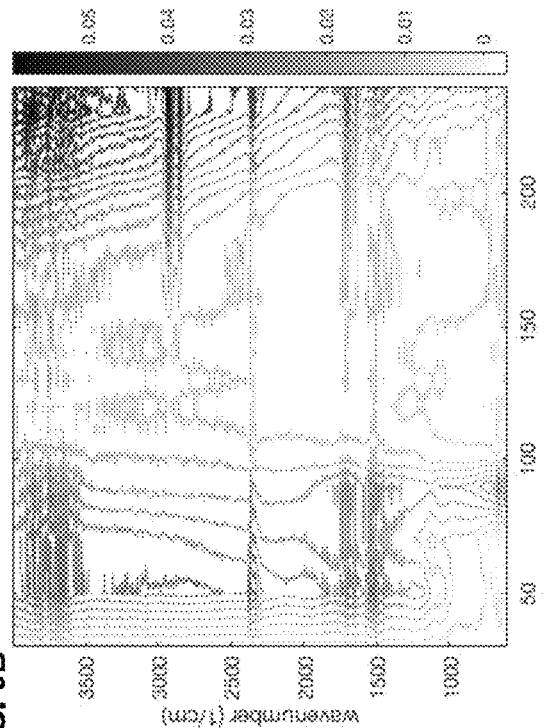
FIGS. 9A and 9B compare the contour plots for two different roasts, showing the correlated holistic evolution of both the spectral peaks and the uneven vertical shift, which contain complementary diagnostic information, with color versions provided in FIGS. 9C and 9D.
Figure 9B:
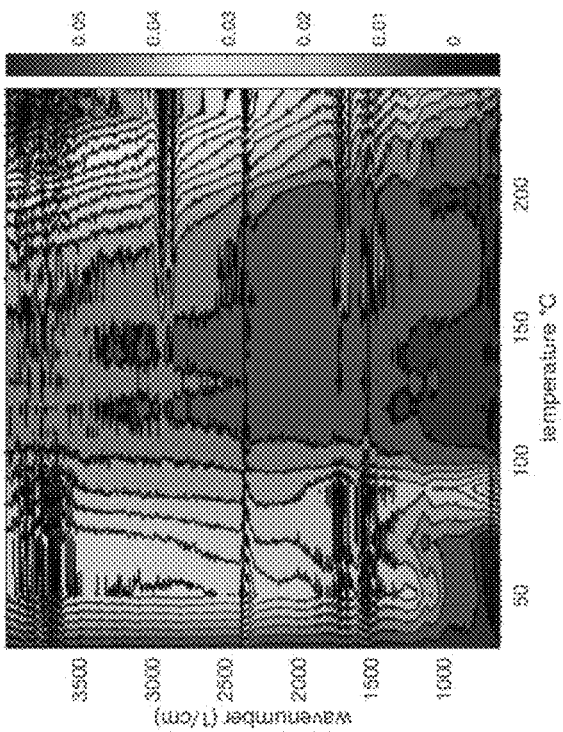
Figure 9C:
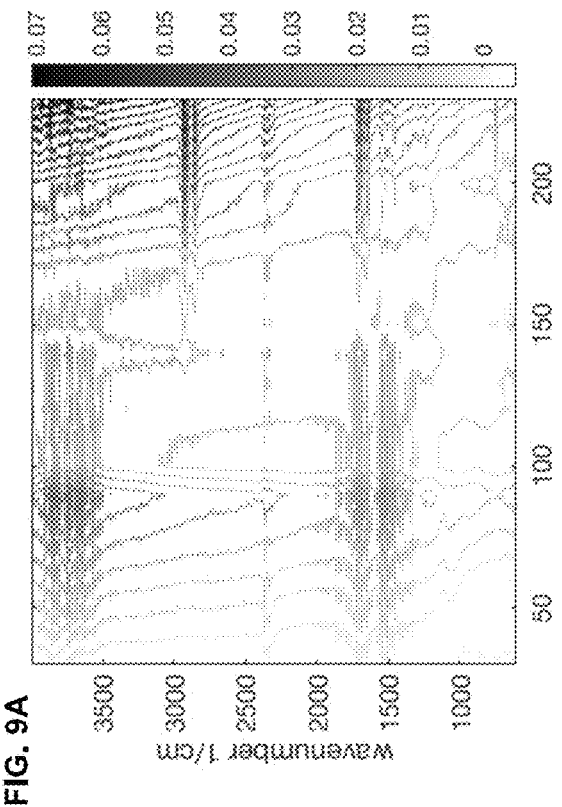
Figure 9D:
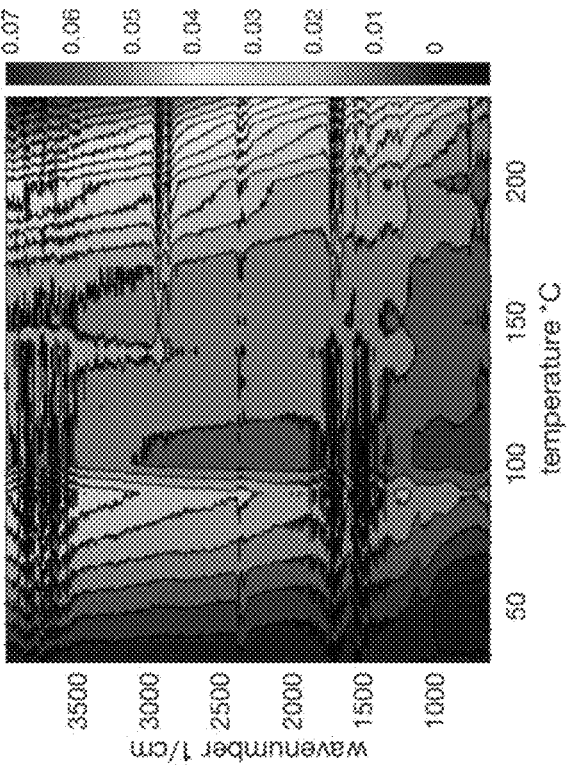

FIGS. 9A and 9B compare the contour plots for two different roasts, showing the correlated holistic evolution of both the spectral peaks and the uneven vertical shift, which contain complementary diagnostic information. Color versions of FIG. 9A and FIG. 9B are provided in FIG. 9C and FIG. 9D, respectively.

Example 2 presents analysis of the FTIR spectra of a 4-bean roast acquired with the same experimental setup as Example 1, but with a single background acquired at 30° C. was applied to all the spectra. FIGS. 10-13 show the global evolution of the raw FTIR data and the uneven vertical shift of the spectra, while FIG. 14 illustrates the effect of the derivative of the intensity with respect to temperature for a wavenumber region in which multiple signatures exist in proximity. Results were confirmed with correlation plots of portions of the spectrum with respect to reference spectra at different temperatures, and peak area calculations for small wavenumber bins that avoid inclusion of multiple signatures.

FIGS. 10 through 14 correspond to Example 2.

Figure 10:
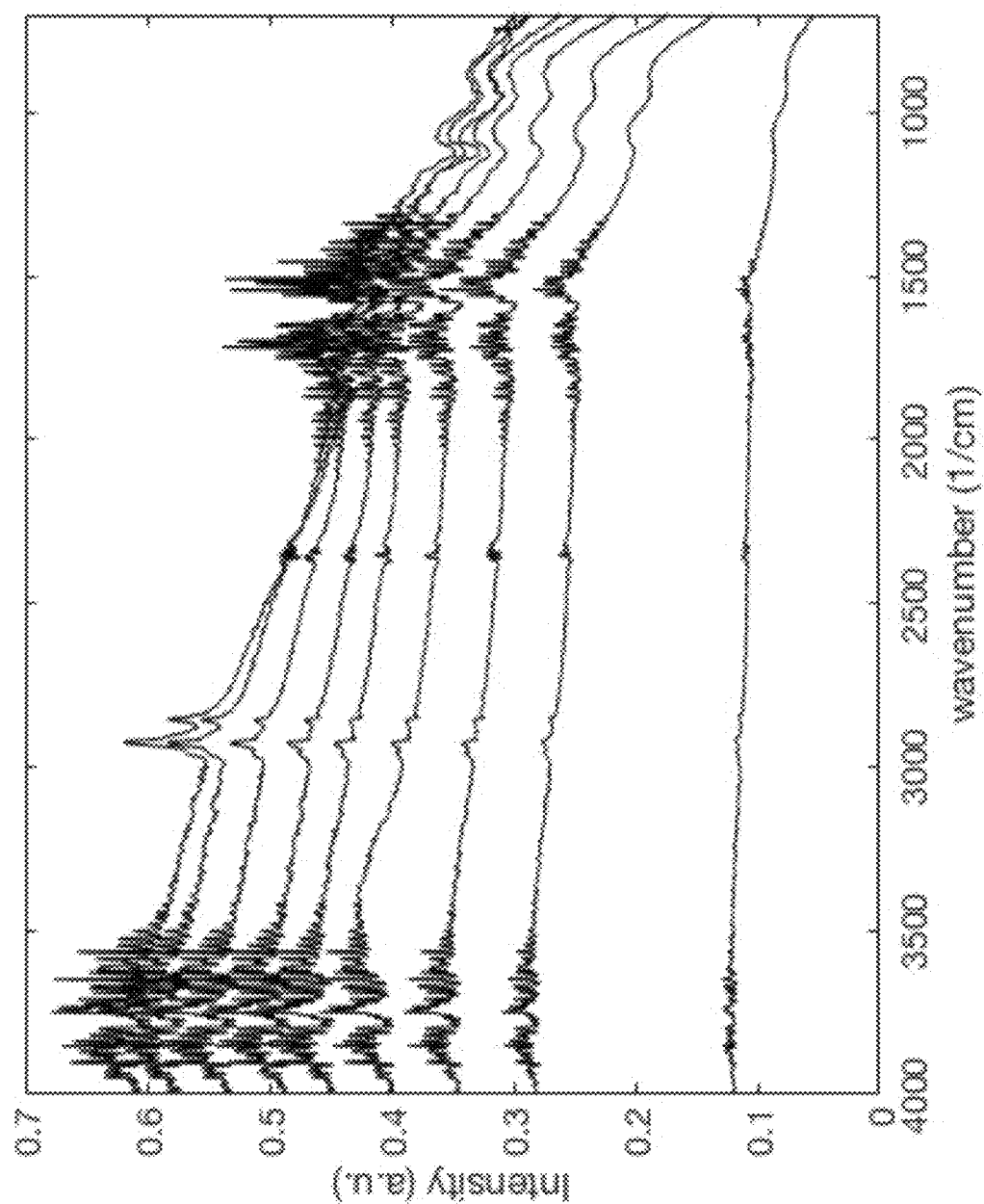
FIG. 10 is a second example of a series of mid-IR absorption spectra acquired during roasting with the temperatures indicated in ° C., for an alternate approach to background subtraction (Example 2)

FIG. 10 is a second example of a series of mid-IR absorption spectra acquired during roasting with the temperatures indicated in ° C., where a single background was acquired at 30° C. and applied to all of the spectra.

Figure 11:
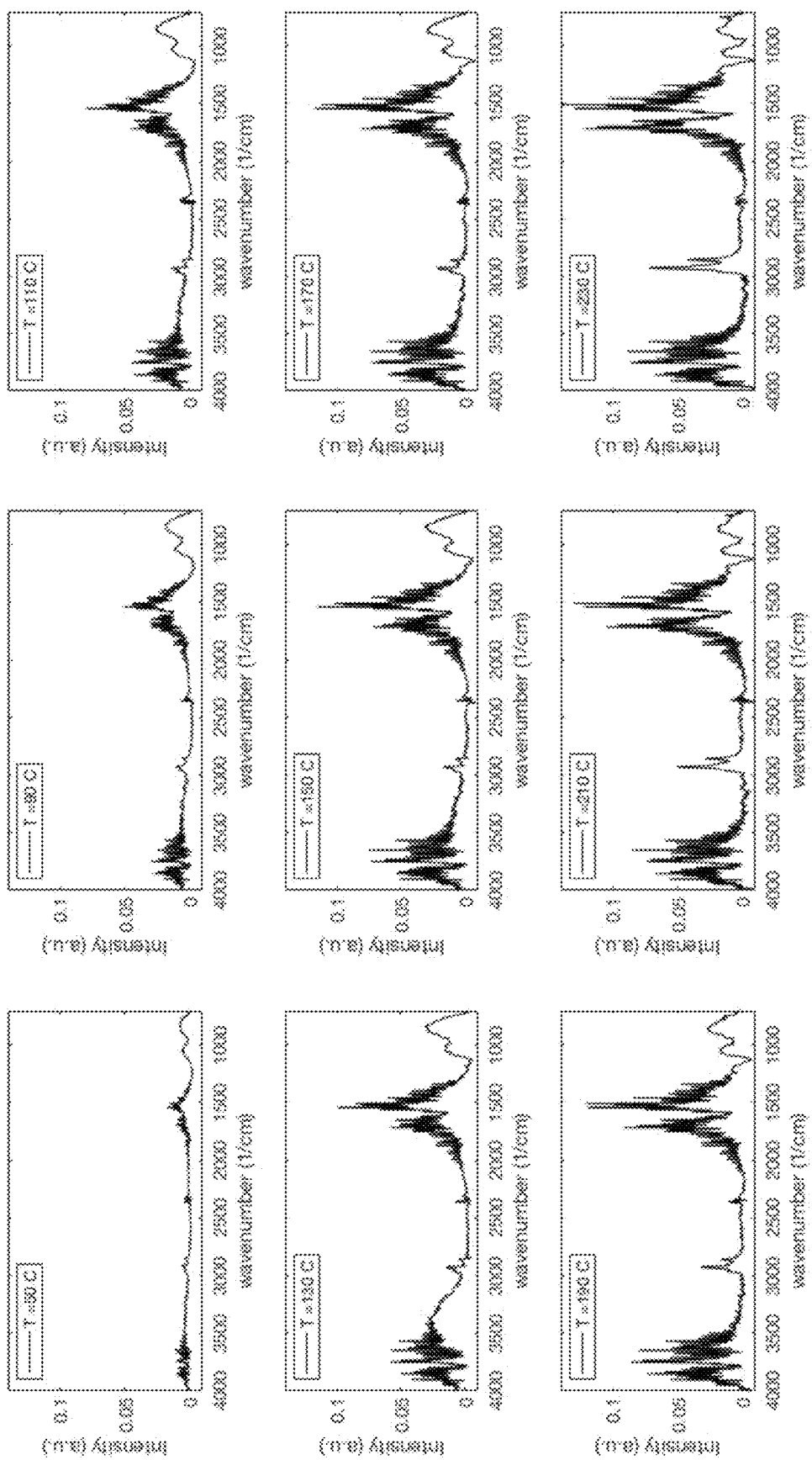
FIG. 11 shows a series of mid-IR absorption spectra at different temperatures of the gases emitted during roasting after baseline removal of the even vertical shift for each spectrum for Example 2.

FIG. 11 shows mid-IR absorption spectra at different temperatures of the gases emitted during roasting after baseline removal of the even vertical shift for each spectrum for Example 2.

Figure 12:
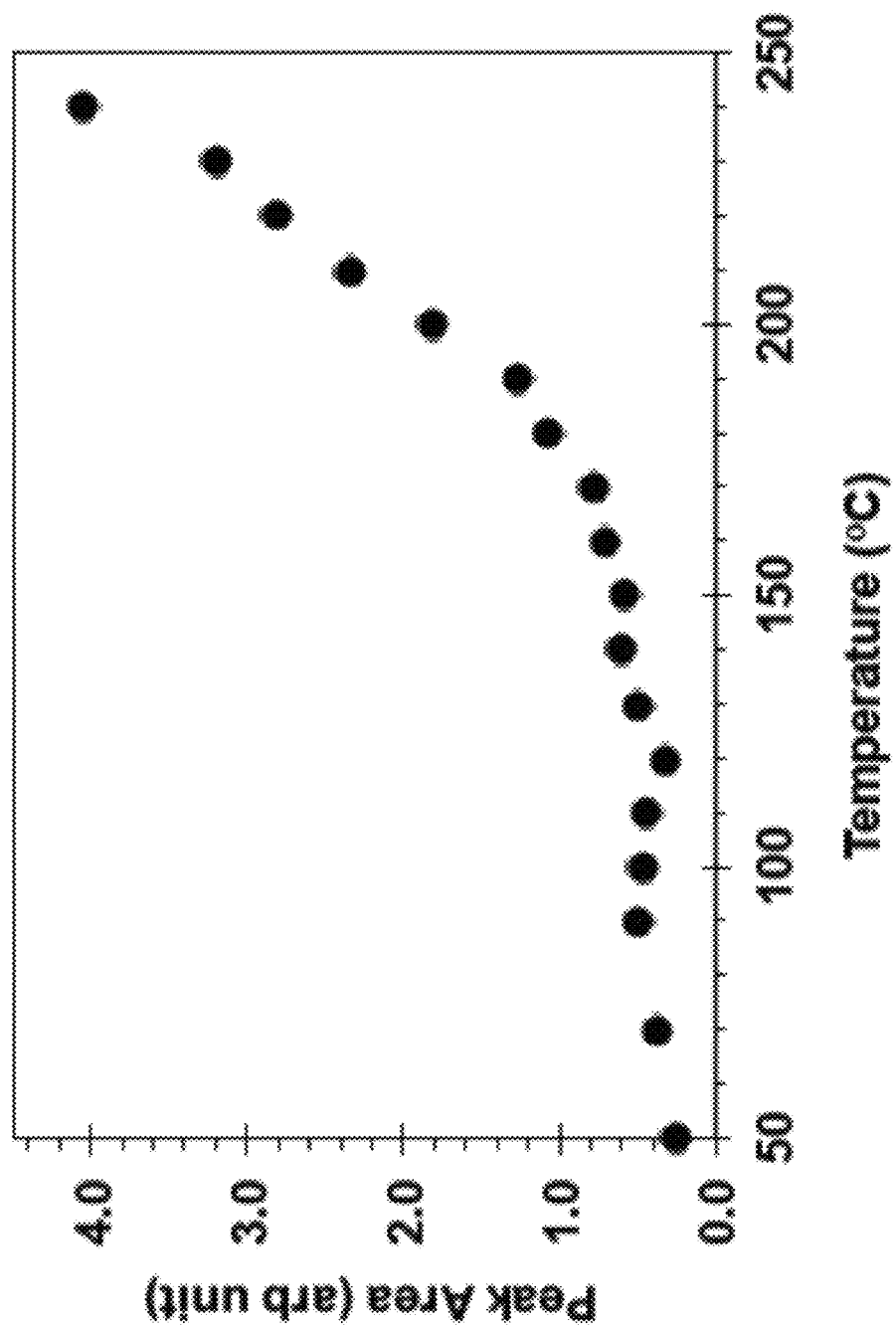
FIG. 12 is a graph of the intensity of the signals as calculated from the area under the peaks between 2985 and 2831 cm-1 for Example 2.
Figure 13A:
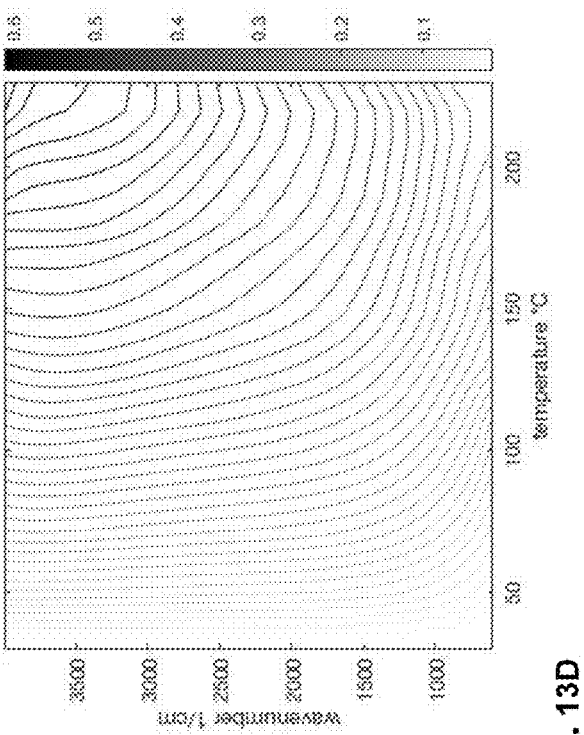
FIGS. 13A-13D is the equivalent of FIGS. 7A-7D, for Example 2, respectively.
Figure 13B:
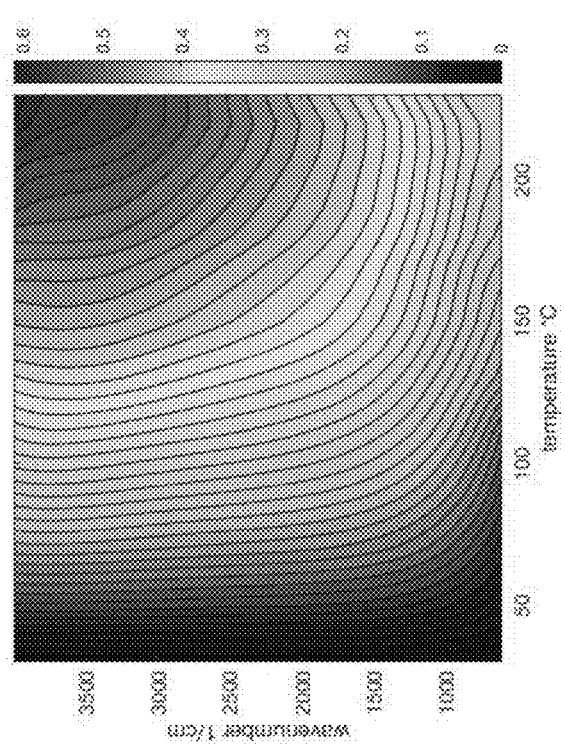
Figure 13C:
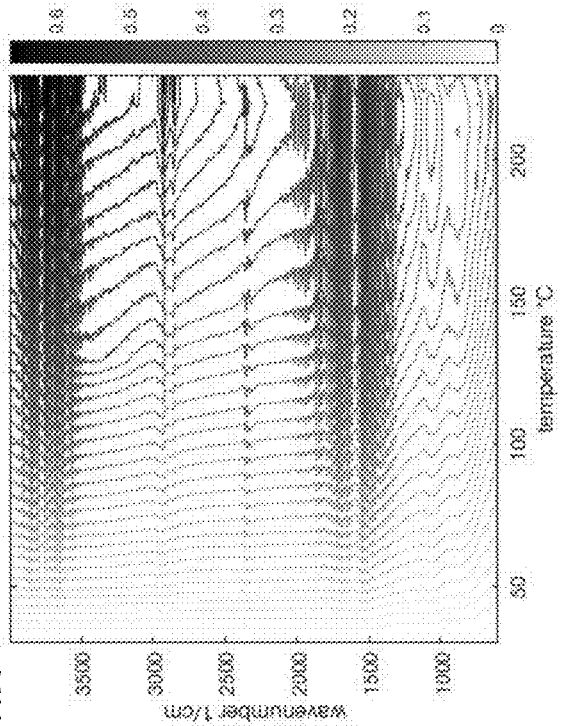
Figure 13D:
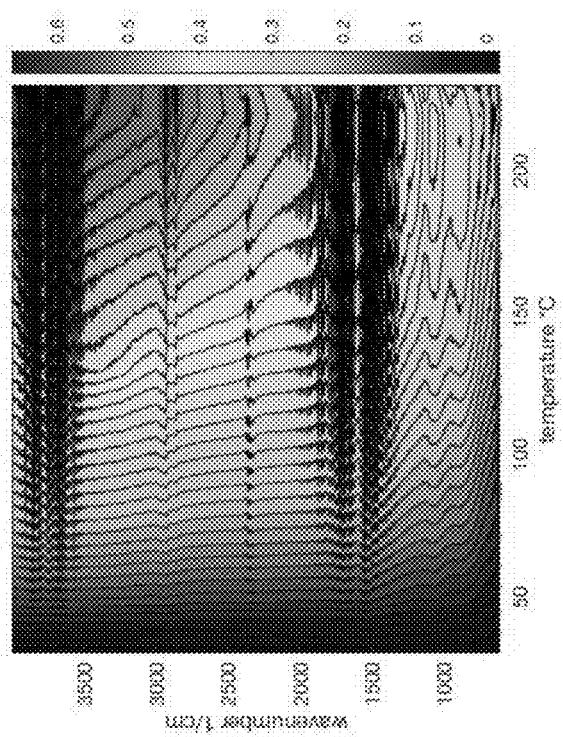

FIG. 12 is a graph of the intensity of the signals as calculated from the area under the peaks between 2985 and 2831 cm-1 for Example 2.

FIG. 13 is the equivalent of FIG. 7, for Example 2.

FIG. 14A is a graph of the intensity of the absorption as calculated from the area under the peaks between 1726 and 1691 cm-1 for Example 2. FIG. 14B/14D show the contour plot of the intensity of the absorption for each wavenumber bin as a function of temperature. FIG. 14C/14E show the derivative of the intensity with respect to temperature, which improves the discernment of multiple signatures in the spectrum, including the onset of roasting over FIGS. 14A, 14B and 14D for the background subtraction method used in Example 2. Color versions of FIG. 14B and FIG. 14C are shown in FIG. 14D and FIG. 14E, respectively.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A method for roasting a food item, comprising:
   heating the food item over time to obtain a flavor that accompanies physical and chemical changes in the food item, including an emission of gases;
   subjecting the emitted gases to mid-infrared electromagnetic radiation or visible light;
   measuring a molecular interaction of the mid-infrared electromagnetic radiation or visible light with the emitted gases as a function of at least one roasting parameter to detect spectral changes that accompany the roasting;
   comparing the spectral changes that occur during a specific roasting profile to identify at least one of inception of the roasting, progress of the roasting and maturity of the roasting; and
   adjusting the at least one roasting parameter to achieve a roast of the food item based on the spectral changes.

2. The method of claim 1, wherein the food item comprises coffee, cocoa, beans, nuts, grains or seeds.

3. The method of claim 1, wherein the at least one roasting parameter comprises at least one of temperature or time.

4. The method of claim 1, wherein the spectral changes are mid-infrared spectra in a range of 4000 cm-1 to 400 cm-1 and comprise absorption or transmission of the electromagnetic radiation by the emitted gases.

5. The method of claim 1, wherein comparing the spectral changes comprises evaluating an intensity of signals between 1726 cm-1 and 1690 cm-1 to mark at least one of the inception of the roasting, a level of a roast, the progress of the roasting and the maturity of the roasting.

6. The method of claim 1, wherein comparing the spectral changes comprises evaluating an intensity of signals between 2200 cm-1 and 2000 cm-1 to mark at least one of the inception of the roasting, a level of a roast, the progress of the roasting and the maturity of the roasting.

7. The method of claim 1, wherein comparing the spectral changes comprises evaluating an intensity of signals between 3000 cm-1 and 2800 cm-1 to mark at least one of the inception of the roasting, a level of a roast, the progress of the roasting and the maturity of the roasting.

8. The method of claim 1, wherein comparing the spectral changes comprises evaluating an intensity of signals between 3500 cm-1 and 3100 cm-1 to mark at least one of the inception of the roasting, a level of a roast, the progress of the roasting and the maturity of the roasting.

9. The method of claim 1, further comprising measuring Raman scattering on the emitted gasses during the roasting to identify at least one of the inception of the roasting, a level of a roast, the progress of the roasting and the maturity of the roasting.

10. The method of claim 1, further comprising conducting a holistic evaluation of an evolution of diagnostic features of signals and/or functions of the signals as the signals and/or functions of the signals change with the at least one roasting parameter, wherein a holistic view of the roasting shows a morphological signature of a particular roast.

11. The method of claim 1, further comprising applying mid-infrared measurements of the emitted gases during the roasting to provide calibration information for other sensors and diagnostic outputs.

12. The method of claim 1, further comprising applying mid-infrared measurements of the emitted gases during the roasting to identify at least one of the inception of the roasting, the progress of the roasting and the maturity of the roasting and providing fiducial information in tandem with other sensors.

\* \* \* \* \*